United States Patent [19]
Bacehowski

[11] 4,152,184
[45] May 1, 1979

[54] METHOD OF MANUFACTURING A BLOOD BAG FOR USE IN A TEST FOR NEUTROPHIL MARROW RESERVES

[75] Inventor: David V. Bacehowski, Wildwood, Ill.

[73] Assignee: Baxter Travenol Laboratories, Inc., Deerfield, Ill.

[21] Appl. No.: 769,993

[22] Filed: Feb. 18, 1977

[51] Int. Cl.$^2$ .............................................. B29C 27/00
[52] U.S. Cl. .................................. 156/84; 29/157 R; 29/428; 128/214 D; 128/272; 156/70; 156/183; 156/205; 156/303.1; 264/230; 264/248; 264/295; 264/342 R
[58] Field of Search .................. 128/272, 272.1, 272.3, 128/2 F, DIG. 24, 214 D, 214.2; 150/8; 23/258.5 R; 210/321 R, 493 M, 493 R, 493 B; 113/116 Y, 116 Z; 264/296, 322, 320; 206/390

[56] References Cited

U.S. PATENT DOCUMENTS

| | | | |
|---|---|---|---|
| 3,370,710 | 2/1968 | Bluemle | 210/493 M X |
| 3,411,698 | 11/1968 | Reynolds | 206/390 X |
| 3,550,839 | 12/1970 | Clayton | 229/55 |
| 3,712,033 | 1/1973 | Gronholz | 210/493 R X |
| 3,827,562 | 8/1974 | Esmond | 210/321 R X |
| 3,849,314 | 11/1974 | Niccum et al. | 210/493 |
| 3,948,777 | 4/1976 | Murata et al. | 210/321 R |

OTHER PUBLICATIONS

*Clinical Research*, Abstract by Woodward et al., vol. 21, p. 56 (1973).
*Journal of Laboratory and Clinical Medicine*, vol. 87, No. 6, pp. 1075–1086 (Jun. 9, 1976).

*Primary Examiner*—Robert W. Michell
*Assistant Examiner*—Michael H. Thaler
*Attorney, Agent, or Firm*—Henry W. Collins; Garrettson Ellis; Paul C. Flattery

[57] ABSTRACT

A flexible, collapsible blood bag which defines an access port at one end thereof. The blood bag contains cellophane film of sufficient area to process blood or plasma placed in the bag, so that reinfusion of the blood to a normal donor, after an appropriate residence time in the bag, causes a transient increase in the neutrophil count of the donor's blood. The cellophane film in the bag is folded in an ordered manner, to define generally parallel flow channels having ends positioned adjacent the access port. A screen member may be positioned between the cellophane film and the access port to prevent blocking thereof by the cellophane film. Also, the cellophane film may define a large plurality of raised surface portions, relative to the normal plane of the film, to facilitate the spacing of adjacent, folded layers of the film from each other. This facilitates the definition of the flow channels for blood distribution throughout the cellophane film.

3 Claims, 4 Drawing Figures

METHOD OF MANUFACTURING A BLOOD BAG FOR USE IN A TEST FOR NEUTROPHIL MARROW RESERVES

BACKGROUND OF THE INVENTION

As reported by Brubaker, et al. in the *Journal of Laboratory and Clinical Medicine* Vol, 87, No. 6, pages 1075 to 1086 (June 9, 1976), it may be desired to monitor the capability of a patient, particularly patients undergoing cancer chemotherapy, to release neutrophil blood cells to the bloodstream from bone marrow.

While various tests for this capability presently exist, the cited article discloses a recently-developed test, in which a unit of blood is exposed to the cellophane found in a hemodialysis coil for about fifteen minutes, in conjunction with heparin, and is then reinfused to the patient. The result of this is an abrupt drop in the neutrophil count of the blood, followed within about an hour by a rapid, transient increase in the blood neutrophil count to greater than normal.

This rapid and transient increase in the neutrophil count in the blood is a normal response. Accordingly, patients which fail to show such an increase in the neutrophil count upon such treatment indicate that their neutrophil marrow reserve is inadequate.

In *Clinical Research*, Volume 21, page 56 (1973) an abstract by Woodward and Brubaker is found reporting the use of a specially-made Fenwal brand blood bag containing 0.3 square meter of dialysis coil cellophane in 2250 U.S.P. units of heparin. Stagnation of a unit of animal blood in this bag for fifteen minutes, and the return thereof to the animal, resulted in a transient reduction in the neutrophil count in the blood, followed by an overshoot neutrophilia.

The cellophane-containing blood bag reported in this article was made simply by stuffing, in a generally random manner, the required amount of dialysis coil cellophane (typically Cuprophane, sold by Enka Glanzstoff in Wuppertal, West Germany).

Upon evaluation of these bags, they were found to be unsuitable for human use, because the blood tended to foam excessively as the bags were gently kneaded to obtain good contact between the cellophane and the blood. Also, ai bubbles were trapped in the cellophane, resulting in an undesirable contact between the blood and air.

DESCRIPITON OF THE INVENTION

In accordance with this invention, an improved blood or plasma bag containing cellophane for use in the test of neutrophil marrow reserves is provided.

A flexible, collapsible blood bag which defines at least one access port at one end thereof contains cellophane film of sufficient area to process blood filling the bag, so that reinfusion of the blood to a normal donor after an appropriate length of time, such as fifteen minutes, causes a transient increase in the neutrophil count of the donor.

It has also been found that blood plasma may, if desired, be used in place of blood in accordance with this invention, to achieve similar results. As used herein, the term "blood" is intended to also include cell-free plasma as an equivalent substitute.

The cellophane film in the bag is folded in an ordered manner to define a plurality of generally parallel flow channels, one end of the flow channels being positioned adjacent the access port, to permit the dispersion of blood throughout the cellophane film without foaming and entrapment of bubbles, and permitting the easy removal of essentially all of the blood therefrom for reinfusion.

In accordance with this invention, a screen member is positioned between the cellophane film and the access port, to prevent blocking of the access port by the cellophane film.

Also, the cellophane film may define a large plurality of raised surface portions relative to the normal plane of the film, to facilitate the spacing of adjacent, folded layers of the film from each other, for the improved definition of the flow channels for blood distribution throughout the cellophane film.

While generally at least 0.3 square meter of cellophane film is present in the bag, it is usually preferred for from 0.5 to 3 square meters of cellophane film to be present in the blood bag, when the bag is of a size for processing at least one unit of blood.

The screen member described above may be made of a blood-compatible plastic material and, being a screen member, is of course highly permeable to the flow of fluid therethrough. The screen member preferably defines a U-shaped cross section, and encloses the end of the folded, cellophane film which is adjacent the access port.

The large number of raised portions may be impressed into the cellophane film in any desired manner, for example by constricting and drawing the film as a strip through an orifice, for example, a circular orifice having a radius of about 0.093 inch when using a strip of cellophane four inches wide. This results in the impression of a number of longitudinal creases in the cellophane which, when the cellophane is reopened, serves to provide the slightly-raised surface portions relative to the normal plane of the cellophane film, which prevent adjacent panels of the folded, cellophane film in the blood bag from sticking together so that blood cannot penetrate between the two panels.

In the alternative, cellophane may be heated at a temperature which is slightly below the decomposition temperature of the cellophane, which causes it to shrivel, resulting in another type of slightly raised surface portions, for the purpose of facilitating the spacing of adjacent, folded layers of the cellophane film from each other so that flow channels for blood are made more available.

Referring to the drawings.

Figure 1:
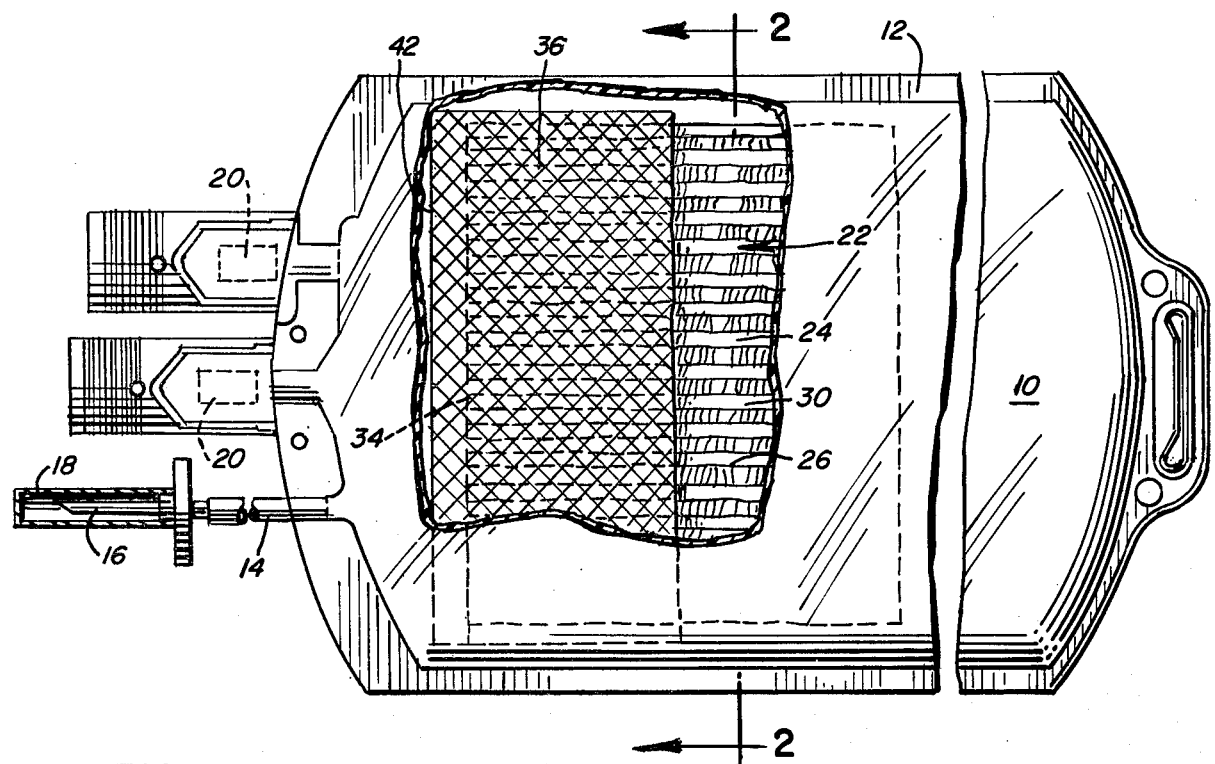
FIG. 1 is a plan view of a blood bag of this invention, with portions broken away for clarity of disclosure.

Referring to the drawings, blood or plasma bag 10 is made from a pair of sheets of blood-compatible plastic such as medical grade polyvinylchloride, polypropylene, or the like, heat sealed at its periphery 12 to define a closed container. Flow tubing 14 communicates with bag 10 and is terminated with spike 16, which may be sealed with an elongated, removable cap 18. Auxiliary access ports 20, may also be provided to the blood bag, being sealed with a sterile tab seal in a conventional manner.

Figure 2:
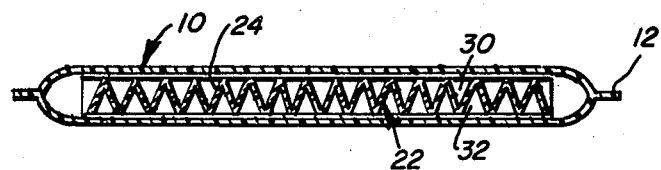
FIG. 2 is a transverse sectional view taken along line 2—2 of FIG. 1.
Figure 3:
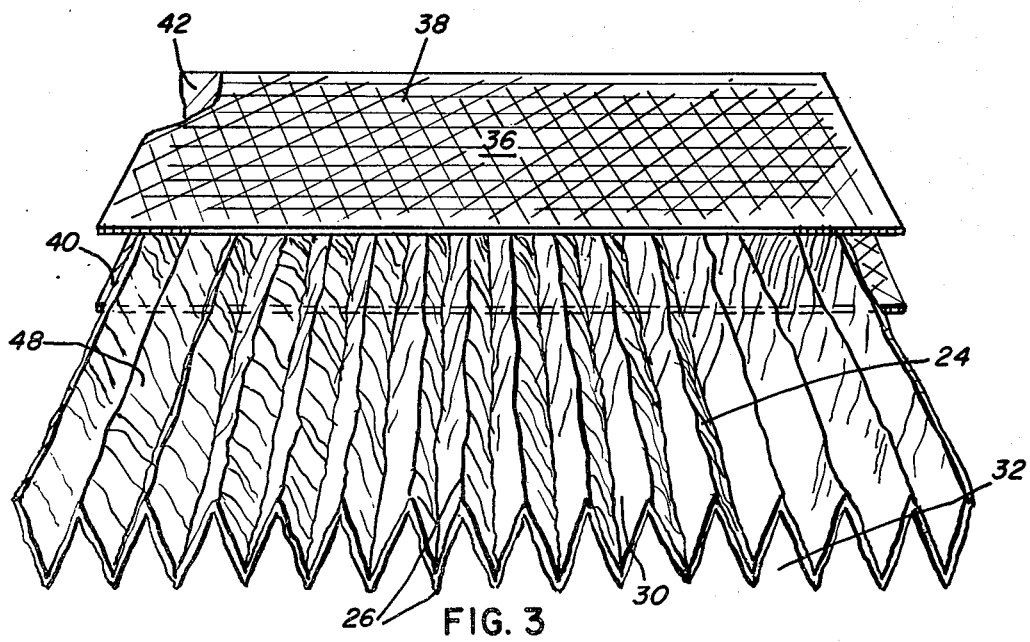
FIG. 3 is an enlarged, perspective view of the screen member and the folded cellophane film which is carried inside a blood bag in accordance with this invention, with a portion broken away for clarity of disclosure.

A folded cellophane strip 22 is sealed in the blood bag. The cellophane strip may be, for example, about four inches wide and about 24 to 48 feet long, pleated or otherwise folded in one half to one inch panels 24, to define an accordion or fan-type fold as shown in FIGS. 2 and 3, in which the separate panels 24 are connected together along fold lines 26, which extend longitudinally along the bag so that their respective ends are positioned adjacent the access ports 14, 20.

Accordingly, flow channels 30, 32 are defined by the pleated structure of cellophane in a longitudinal direction along the bag having ends 34 which are correspondingly adjacent to the access ports 14, 20. Hence, blood may be distributed between the access ports and essentially the entire area of the cellophane 22 via flow channels 30, 32. Air may be expelled from the bag by the same route while it is filling with blood. The air bubbles are easily removed from the bag, and blood may also be completely expelled for reinfusion back to the patient when that is desired.

In this manner, essentially all of the surface area of the cellophane 24 is exposed to the blood.

Alternatively, other folding patterns for the cellophane may be used, such as a sprial fold pattern. Cuprophane brand cellophane is the generally preferred type for use.

Normally, when bag 10 is empty, the cellophane 22 will tend to be flattened from the idealized configuration shown in FIGS. 2 and 3, the various pleated panels overlying each other in a collapsed form. However, when the bag is filled with blood the cellophane tends to assume the pleated configuration which is illustrated herein.

The number of pleats in the drawings have been reduced from that which may be actually used, for simplicity of disclosure. In fact, it is contemplated that about 192 pleats (i.e. pairs of panels 24) may be utilized per bag in the case, for example, of a 4 inch strip of cellophane which is about 24 feet long (i.e. an area of about 8 sqaure feet or ¾ square meter), each panel 24 being ¾ inch wide.

In accordance with this invention, a screen member 36 is provided which may be made of Saran (poly(vinylchloridevinylidene chloride)) or an equivalent material, being about 4¾ inches wide and 4 inches long. This screening material may be folded along a line parallel to its wider dimension to provide a pair of sections 38, 40 which may be about 2 inches wide, or slightly less, connected together at an area of folding 42, to provde a receptacle of U-shaped cross section for the pleated cellophane, as specifically shown in FIG. 3. This prevents the cellophane from clogging the access ports 14, 20 and restricting flow communication in and out of the bag 10.

Cellophane strip 22 may also define a large plurality of slightly raised surface portions, specifically shown to be wrinkles 48 extending transversely to fold lines 26. Wrinkles 48 may be formed, as stated before, by drawing the strips through a constricted orifice or the like. In the alternative, the cellophane may have been heated at a temperature below its decomposition temperature to cause the material to shrivel.

Wrinkles 48 or other surface discontinuities provide sufficient irregularity between adjacent panels 24 of the cellophane so that panels 24 tend not to stick together tightly, blocking the entry of blood between them.

Accordingly, essentially all of both sides of the area of the cellophane 22 can be made available to the access of blood, flowing through channels 30, 32 to and from the cellophane, for treatment of the blood.

After collection in bag 10, and a desired induction period, the blood can be reinfused to the patient, and the neutrophil content of the blood monitored as a test of neutrophil marrow reserves.

Figure 4:
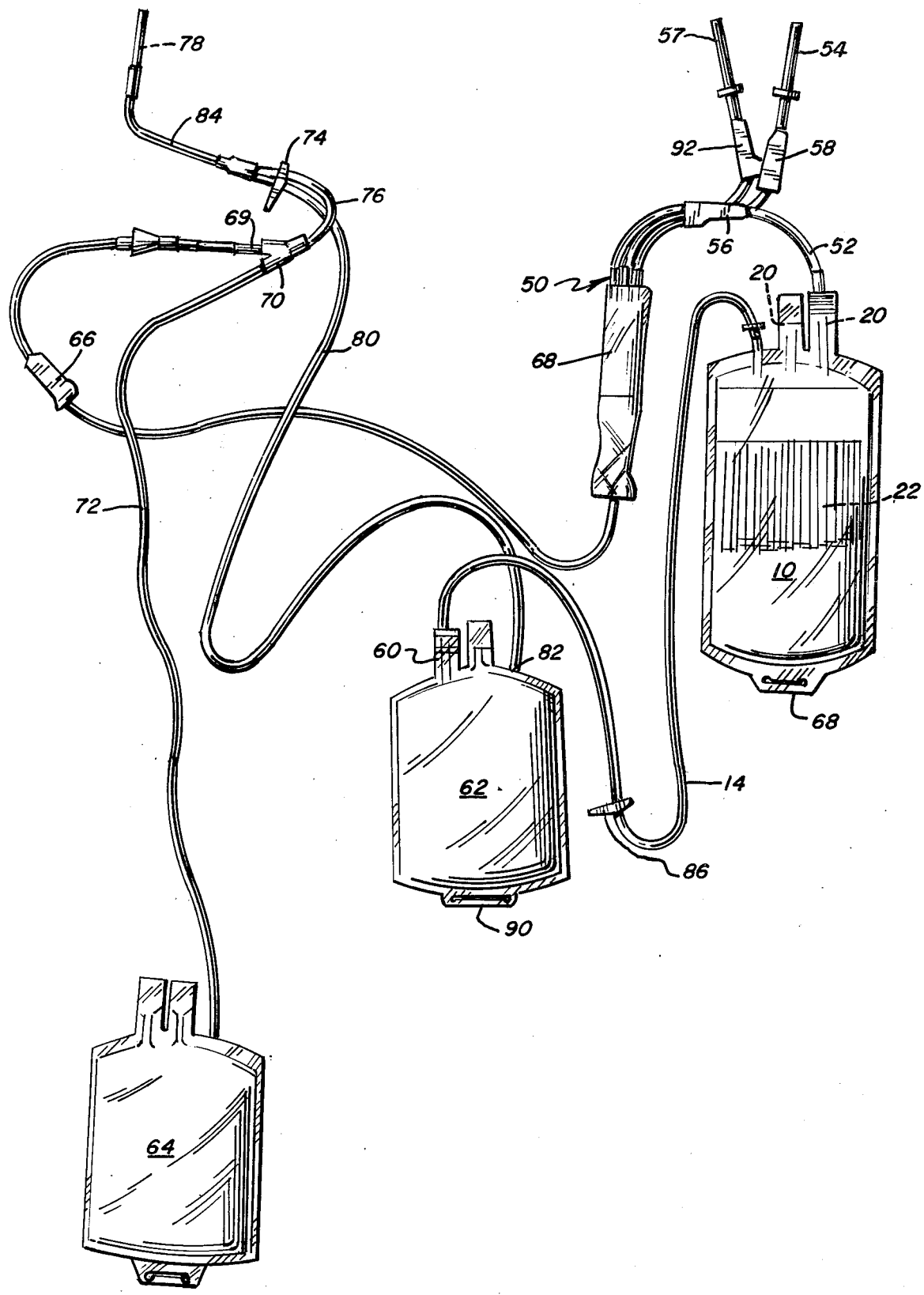
FIG. 4 is a plan view of a disposable neutrophil test system, including the bag of FIGS. 1 and 3.

FIG. 4 shows a typical multiple bag system, utilizing bag 10, for use in the neutrophil marrow test. Bag 10 is shown as a separate unit, but, alternatively, it may be integrally joined with the remaining components of the set. The following is a description of the multiple bag set of FIG. 4, along with a discussion of how it may be used.

A triple-lead blood-solution recipient set 50 (manufactured for example by the Fenwal Division of Baxter Travenol Laboratories, Inc.) is shown. Set 50 has leads 52, 54, 57, each of which carries a penetrating spike which is sealed in a removable closure. The spike of lead 52 is opened, and passed through one of the access ports 20 of bag 10.

Lead 54 may be connected to a source of sterile saline injection solution. (Not shown). Clamps 56 and 58 on leads 52 and 54, are closed.

Flow tubing 14 is shown to be connected to an access port 60 of a blood bag 62, which is preferably part of a double bag system, including blood bag 64 and connecting tubing as shown and described below. Bag 62 contains an anticoagulent solution such as heparin to prevent blood clotting. If desired, the multiple bag system may be a Fenwal Heparin Double Plasmapheresis BLOOD PACK ® unit, which is commercially available at the present time, or any other appropriate multiple-bag system.

Clamp 66 of set 50 is also closed to prevent fluid flow therethrough at the initial stage of operation.

Clamps 56 and 58 are then opened to allow saline solution to pass through lead 54 into filter chamber 68, and from there through lead 52 into bag 10, until approximately one third of a liter of saline solution has entered bag 10. Then, clamps 56, 58 are again closed.

Bag 10 is kneaded in order to wet the full surface of the cellophane film with the saline solution, until the film has been completely softened and rendered pliable. Then, bag 10 is suspended from an IV pole, by hanger 68, in inverted position.

The spike 69 of set 50 is connected into Y-site 70 of the double-bag system of bags 62, 64. Then, clamps 56 and 66 are opened to allow the saline solution to drain through lead 52 and set 50 into flow tubing 72, and into bag 64. Clamp 74, which may be a slide clamp, seals the flow tubing 76 which communicates with Y-site 70.

Then, the clamps are all closed, and tubing 72 is sealed or clipped in two spaced places and severed between them, so that bag 64, containing the saline wash solution, may be removed and discarded without opening the sterile system.

Lead 52 is also sealed with spaced seals and severed as well, with the coupling end of lead 52 remaining in position in bag 10 to retain a sterile seal.

Blood bag 62 is suspended as far as possible below the donor's arm. The cover of needle 78 is removed, and phlebotomy is accomplished in a vein of the donor's arm with needle 78. A blood pressure cuff may be used if desired.

Donor tubing 80 is opened by removal of the conventional bead from its end 82, and blood is allowed to flow through tube 80 into bag 62, which contains the anticoagulant, with frequent gentle mixing of the blood and anticoagulant.

After collection, blood may be flushed out of the tube 80 with saline solution from lead 54 of set 50 by opening clamps 66 and 58, regulating the flow of saline to a slow drip. Also, through the remaining part of the process, a slow drip of saline may be administered through needle 78 to maintain its patency.

At this time in the process, the coupler or spike of transfer tubing 14 of bag 10 may then be inserted into an access site 60 of bag 62, as shown in FIG. 4. It may also be inserted at an earlier stage of the process if desired. Tubing 14 is clamped with a hemostat or a slide clamp 86, which may now be opened. Bag 62 is inverted over bag 10 and hung vertically from hanger 90, to allow the heparinized blood to pass through tubing 14 into bag 10. Tubing 14 may then be sealed in two places and severed. Bag 10 may then be gently inverted several times to mix the blood thoroughly into intimate contact with the cellophane film.

Bag 10 is placed in a protective overwrap, and may be incubated at an appropriate temperature and time, for example in a 37° C. water bath for fifteen minutes. During this time, the blood in the remaining segment of tubing 14 attached to bag 10 is "stripped" into bag 10 by use of a Fenwal tube stripping device or the like. Blood from bag 10 is allowed to flow back into the remaining segment of tube 14 attached to bag 10, after which a portion of the tubing may be sealed with another spaced seal and severed from bag 10, to obtain a blood sample. The blood sample may then be conventionally tested for hemolysis, prior to infusion of the blood back to the patent.

After the fifteen minute induction period, bag 10 is removed from the water bath, and lead 57 of set 50 is connected to the remaining access port 20 of bag 10. Clamp 58 is closed to stop the saline flow, and clamps 92, 66, and 74 are opened, after suspending bag 10 from an IV pole in inverted position, to reinfuse the blood through set 50, tubing 84, and needle 78 back to the patient. Infusion should take approximately 10 minutes.

When the blood has been reinfused, clamp 58 is once again opened to flush the set with saline, to return the remaining traces of blood to the patient. Then all clamps are closed, the phlebotomy needle 78 removed from the patient, and the apparatus disclosed.

Additional blood samples may be drawn from the patient fourteen minutes after the start of reinfusion, and then gain at 30, 45, and 60 minutes after reinfusion. A neutrophil count is made on each blood sample, to determine the presence or absence of the normal overshoot neutrophilia.

While the arrangement of FIG. 4 is shown as one method of utilizing the invention of this application, other arrangements are equally possible. In particular, it has been determined that it is not necessary to place whole blood into the cellophane-containing bag of this invention in order to obtain the overshoot neutrophilia upon reinfusion to a patient. Blood plasma, after an exposure to cellophane in the bag of this invention, similar to the exposure conditions described above, provides a similar effect in a normal, healthy patient.

Accordingly, if desired, the bag of this invention may be utilized in conjunction with a plasmapherisis set of a type which is conventionally sold by the Fenwal division of Baxter Travenol Laboratories, Inc. Also, plasmapherisis apparatus may be appropriately modified as desired by the addition of an integrally attached bag of this invention.

Specifically, the bag of this invention may be integrally connected with a companion blood bag which, in turn, is connected to a phlebotomy needle by donor tubing which carries a Y-site. Blood is then collected into the companion bag of the bag of this invention, which companion bag contains an anticoagulant such as heparin, and both the companion bag and the bag of this invention may be centrifuged to settle the cells. Thereafter, the plasma may be administered through the connecting tubing from the companion bag to the bag of this invention, and the cells reinfused from the companion bag after being suspended in saline, which can be administered by a conventional blood set through the Y-site. Then, after separation of the bag of this invention and an appropriate period of induction, the plasma may be reinfused to the patient by connection of the bag of this invention with another lead of the same blood set.

The above has been offered for illustrative purposes only, and is not intended to limit the invention of this application, which is as defined in the claims below.

That which is claimed is:

1. The method of manufacturing a blood bag which has an access port and contains folded cellophane film, which comprises impressing into said cellophane film large numbers of raised surface creases relative to the normal plane of said film by transversely constricting said film relative to the longitudinal axis of said film to form longitudinal creases, and thereafter allowing said film to re-expand to its normal transverse width; folding said cellophane film strip to define a plurality of overlying panels connected together by fold areas, to define a plurality of parallel flow channels between said channels; and sealing said folded cellophane film into a blood bag whereby the cellophane film is retained in folded condition.

2. The method of claim 1 which includes the step of placing a screen member adjacent one end of said folded cellophane film between said one end of the cellophane film and said access port.

3. The method of manufacturing a blood bag which contains folded cellophane film, which comprises, impressing into said cellophane film a large number of raised surface creases relative to the normal plane of said film by exposing said film to sufficient heat to cause it to shrivel; folding said cellophane film strip to define a plurality of overlying panels connected together by fold areas, to define a plurality of parllel flow channels between said channels; and sealing said folded cellophane film into a blood bag whereby the cellophane film is retained in folded condition.

* * * * *